United States Patent [19]

Eyer

[11] Patent Number: 5,144,057

[45] Date of Patent: Sep. 1, 1992

[54] PROCESS FOR THE PRODUCTION OF 3-OXOCARBOXYLIC ACID ESTERS

[75] Inventor: Martin Eyer, Glis, Switzerland

[73] Assignee: Lonza Ltd., Gampel/Valais, Switzerland

[21] Appl. No.: 774,876

[22] Filed: Oct. 11, 1991

[51] Int. Cl.$^5$ .............................................. C07C 69/76
[52] U.S. Cl. ......................................... 560/51; 560/9; 560/125; 560/126; 560/174
[58] Field of Search .................. 560/51, 174, 125, 126, 560/9

[56] References Cited

FOREIGN PATENT DOCUMENTS 57-70837 5/1982 Japan .

OTHER PUBLICATIONS

C. R. Hauser and B. E. Hudson, Jr., "Organic Reactions", vol. 1 (1942) pp. 297 to 302.
G. Heese, "Methoden der organischen Chemie", [Methods of Organic Chemistry], vol. VI/1d, 4th Ed., (1978), p. 73.
B. M. Conrad, Justus Liebigs Ann. Chem., 188, (1877), pp. 296–274.
H. Henecka, "Methoden der organischen Chemie", 4th Ed., vol. VIII (1952), pp. 615 and 616.

*Primary Examiner*—Paul J. Killos
*Attorney, Agent, or Firm*—Fisher, Christen & Sabol

[57] ABSTRACT

3-Oxocarboxylic acid esters are produced by acylation of the magnesium enolates of acetoacetic acid esters with carboxylic acid chlorides and cleavage of the acetyl group from the acylacetoacetic acid esters formed as the intermediate product. The yields and purity of the products are considerably improved by adding a tertiary amine during the acylation.

17 Claims, No Drawings

PROCESS FOR THE PRODUCTION OF 3-OXOCARBOXYLIC ACID ESTERS

BACKGROUND OF THE INVENTION

1. Field Of The Invention

The invention relates to a process for the production of 3-oxocarboxylic acid esters from acetoacetic acid esters.

2. Prior Art

3-Oxocarboxylic acid esters (acylacetic acid esters) of the general formula:

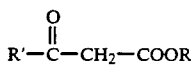
(1)

are extraordinarily important and versatile intermediate products. This fact is attributable to the numerous different reaction possibilities of these compounds. Their coupling with aromatic diazonium salts thus yields 2-(arylhydrazono)-3-oxocarboxylic acid esters, which are used as dyes, for example, in photographic materials.

With hydrazines, the 3-oxocarboxylic acid esters cyclize to pyrazolones, of which several are valuable pharmaceutical active ingredients. Halogenated benzoylacetic acid esters (R' is substituted phenyl) are initial products for quinolone and cinnolinecarboxylic acids, which can be used, for example, as antibiotics (e.g., ciprofloxacin).

3-Oxopentanoic acid ester (R' is ethyl) is an important intermediate product for the synthesis of the antiinflammatory active ingredient etodolac.

Numerous methods for the production of 3-oxocarboxylic acid esters have been known for some time. For example, C.R. Hauser and B.E. Hudson, Jr. provide a survey in Orqanic Reactions, Vol. 1, (1942), pages 297 to 302.

In particular, the acylation of malonic esters or acetoacetic acid esters with carboxylic acid chlorides with subsequent cleavage of an ester group or an acetyl group is generally applicable {see, G. Hesse in "Methoden der organischen Chemie" [Methods of Organic Chemistry], 4th ed., Vol. VI/1d, (1978), page 73}.

For reasons of cost, acetoacetic acid ester is to be preferred as the initial material for the production on an industrial scale. In this case, the acetoacetic acid ester is advantageously used in the form of a metal enolate. For this purpose, magnesium enolates, which can easily be produced even in an aqueous medium, are especially suitable [see, e.g. B.M. Conrad, Justus Liebigs Ann. Chem., 188, (1877), pages 269 to 274].

Another advantage of the use of acetoacetic acid esters instead of malonic esters as the initial material is the simpler cleavage, in comparison to acylmalonic esters, of the 2-acyl- acetoacetic acid esters resulting as the intermediate product [see, H. Henecka in "Methoden der organischen Chemie", 4th ed., Vol. VIII, (1952), pages 615 ff], which can take place, for example, with aqueous ammonia.

However, it has been shown that the acylation of acetoacetic acid ester magnesium enolate with carboxylic acid chlorides in practice often leads to unsatisfactory results. Thus, in particular, by-products, such as, diacetoacetic ester, are often obtained, which not only reduce the yield of the desired product but are also difficult to separate and, thus, result in unjustifiable expense in the working up or make the extraction of a pure product completely impossible.

For example, the reworking of the process for the production of pivaloylacetic acid ethyl ester from acetoacetic ester magnesium enolate and pivaloyl chloride, described in published Japanese Published Pat. Application No. 57-70837, yielded only usable yields of about 35 percent and a very unpure product with a content of only about 70 percent.

BROAD DESCRIPTION OF THE INVENTION

The main object of the invention is to provide a process for the production of 3-oxocarboxylic acid esters of the general formula:

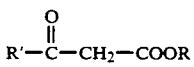
(1)

from the corresponding acetoacetic acid ester magnesium enolates and the corresponding carboxylic acid chlorides which, for a large number of different types of radicals R and R', yield the desired products in high yield and purity and is economically feasible on an industrial scale. Other objects and advantages of the invention are set out herein or are obvious herefrom to one skilled in the art.

The objects and advantages of the invention are achieved by the process of the invention.

The invention involves a process for the production of 3-oxocarboxylic acid esters of the general formula:

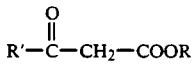
(1)

wherein R means:
a straight-chain or branched alkyl radical with 1 to 20 C atoms,
an alkenyl or alkinyl radical with 3 to 6 C atoms,
a cycloalkyl radical,
an ethyl radical substituted with an alkoxy group with 1 to 4 C atoms,
an alkyl or alkenyl radical with 1 to 4 C atoms substituted with an optionally substituted phenyl group, or
an optionally substituted aryl radical, and
R' means:
a straight-chain or branched alkyl radical with 1 to 20 C atoms, which can be substituted by halogens, lower alkoxy groups, lower alkylthio groups, optionally substituted aryl, cycloalkyl, aryloxy, arylthio or saturated or unsaturated heterocycles, excluding unsubstituted methyl,
a straight-chain or branched alkenyl radical with 2 to 20 C atoms, which can be substituted by halogens or aryl,
an alkinyl radical, which can be substituted by aryl,
an optionally-substituted cycloalkyl or cycloalkenyl radical,
an optionally-substituted monocyclic or polycyclic aryl radical, or
an optionally-substituted saturated or unsaturated monocyclic or polycyclic heterocyclic radical.
The magnesium enolates of the corresponding acetoacetic acid esters of the general formula:

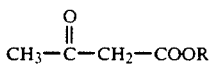
 (2)

are acylated with the corresponding carboxylic acid chlorides of the general formula:

 (3)

to the corresponding 2-acylacetoacetic acid esters of the general formula:

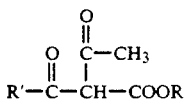 (4)

wherein in each case R and R' have the above-mentioned meanings. The acylation is performed in the presence of a tertiary amine. Subsequently the acetyl group is cleaved.

DETAILED DESCRIPTION OF THE INVENTION

It was found that by adding a tertiary amine during the reaction of the acetoacetic acid ester magnesium enolate with the carboxylic acid chloride, the yield increases considerably and the formation of undesirable by-products can be substantially suppressed.

As the tertiary amine, basically all compounds are to be considered here which have at least one basic nitrogen atom and carry no hydrogen atoms on the nitrogen. This includes in particular: trialkylamines with the same or different straight-chain, branched or cyclic alkyl radicals, such as, trimethylamine, triethylamine, tripropylamine, tributylamine, triisobutylamine, diethylmethylamine, dimethylcyclohexylamine, alkyl(arylalkyl)amines, such as, N,N-dimethylbenzylamine, arylalkylamines, such as, N,N-dimethylaniline or N,N-diethylaniline, compounds in which nitrogen is incorporated in a saturated ring system, such as, N-alkylpyrrolidines, N-alkylpiperidines, N-alkylmorpholines, quinuclidine, 1,4-diazabicyclo[2.2.2]octane ("DABCO"), or else aromatic nitrogen heterocycles, such as, pyridine, quinoline, alkylpyridines, such as, methyl, methylethyl, dimethyl and trimethylpyridines, 4-(dialkylamino)pyridines such as 4-(dimethylamino)pyridine ("DMAP") , as well as amidine-like compounds, such as, 1,5-diazabicyclo[4.3.0]non-5-ene ("DBN") and 1,8-diazabicyclo[5.4.0]undec-7-ene ("DBU"). A trialkylamine is preferably used; triethylamine is especially preferred. The tertiary amine is suitably added in stoichiometric amounts, preferably in amounts of 1.0 to 1.4 mol, relative to 1 mol of magnesium enolate.

As the initial material for the process according to the invention, basically all acetoacetic acid esters of the general formula:

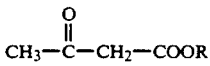 (2)

which form sufficiently stable magnesium enolates are suitable. These ar in particular the esters of straight-chain or branched, primary, secondary or tertiary alkanols with up to 20 C atoms, in which R, in the general formula (2), correspondingly is a straight-chain or branched alkyl radical with 1-20 C atoms, is, for example, methyl, ethyl, butyl, hexyl, dodecyl, octadecyl, isopropyl, isobutyl or tert-butyl, the esters of unsaturated alcohols with 3 to 6 C atoms, in which R, for example, is allyl, beta-methallyl, crotyl, 4-penten-1-yl or propargyl, the esters of cyclic alcohols, in which R, for example, is cyclohexyl, the esters of phenyl-substituted $C_1$-$C_4$ alkanols and $C_1$-$C_4$ alkenols, in which R, for example, is benzyl, phenylethyl or cinnamyl, the esters of ethylene glycol monoalkyl ethers with $C_1$-$C_4$ alkyl groups, in which R, for example, is 2-methoxyethyl, as well as the esters of optionally-substituted phenols, in which R, for example, is phenyl, tolyl or anisyl.

As the acid chlorides, basically all carboxylic acid chlorides of general formula R'-COCl (3) with the exception of unsubstituted acetyl chloride are usable. These are in particular the straight-chain or branched alkanoyl chlorides with up to 21 C atoms, in which R', for example, is ethyl, propyl, butyl, hexyl, octyl, dodecyl, octadecyl, isopropyl, isobutyl, tert-butyl or neopentyl, alkanoyl chlorides, which are substituted by halogens, lower alkoxy groups, lower alkylthio groups, optionally-substituted aryl groups, cycloalkyl groups, aryloxy groups, arylthio groups or saturated or unsaturated heterocyclic radicals, in which, thus, R', for example, is 2-chloroethyl, methoxymethyl, methylthiomethyl, benzyl, phenethyl, p-methoxybenzyl, p-methylbenzyl, cyclohexylmethyl, phenoxymethyl, phenylthiomethyl, pyridylmethyl, tetrahydrofurylmethyl, straight-chain or branched alkenoyl chlorides with up to 21 C atoms, in which R', for example, is vinyl, allyl, isopropenyl, methallyl, crotyl or 8-heptadecen-1-yl, alkenoyl chlorides, which are substituted by halogens or aryl groups, in which R' thus, for example, is 1-chlorovinyl, 2-phenylethenyl, 2-(4-chlorophenyl)- ethenyl, alkinoyl chlorides optionally-substituted by aryl radicals, in which R', for example, is ethinyl, 1-propinyl, 2-propinyl or phenylethinyl, optionally-substituted cycloalkanoyl or cycloalkenoyl chlorides, in which R', for example, is cyclopropyl, cyclobutyl, cyclopentyl, cyclohexyl, 2,2-dimethylcyclopropyl, menthyl, 1-cyclohexenyl, optionally substituted mono- or polycyclic aroyl chlorides, in which R', for example, is phenyl, o-, m- or p-tolyl, xylyl, mesityl, p-methoxyphenyl, p-chlorophenyl, 2,4,6-trifluorophenyl, 1-naphthyl or 2-naphthyl, and chlorides of saturated or unsaturated heterocyclic carboxylic acids, in which R', for example, is 2-pyridyl, 3-pyridyl, 4-pyridyl, 6-chloro-3-pyridyl, 6-hydroxy-3-pyridyl, 5,6-dichloro-3-pyridyl, 6-methyl-3-pyridyl, 4-piperidyl, 2-thienyl, 2-pyrrolidinyl and 2-indolyl.

The acid chloride is suitably used in the stoichiometrically required amount or a small excess, preferably in an amount of 2.0 to 2.5 mol to one mol of the acetoacetic acid ester magnesium enolate.

The acylation of the acetoacetic acid ester magnesium enolate is advantageously performed in a solvent of low to medium polarity. As the solvent, aromatic hydrocarbons, such as, toluene or xylenes, or ethers, such as, dimethoxyethane, tetrahydrofuran, dioxane or tert-butyl methyl ether, are preferably used. Tetrahydrofuran is especially preferred.

The acylation reaction is suitably performed at a temperature of 20° to 140° C., preferably at 60° to 90° C.

The cleavage of the acetyl group from the 2-acylacetoacetic acid ester resulting as the intermediate product, advantageously takes place with a primary or secondary amine or preferably with ammonia. With use of ammonia, the latter is preferably used in an amount of 3 to 5 mol, relative to 1 mol of the acetoacetic acid ester magnesium enolate used in the first stage.

The following examples illustrate the performance of the process according to the invention.

EXAMPLE 1

Benzoylacetic acid ethyl ester 57.9 g (0.2 mol) of acetoacetic acid ethyl ester magnesium enolate in 750 ml of tetrahydrofuran was suspended under nitrogen, 24.3 g (0.24 mol) of triethylamine was added and 57.4 g (0.408 mol) of benzoyl chloride was instilled in 10 minutes. The reaction mixture was refluxed for 2 hours, cooled with ice water and hydrolyzed with 285 ml of 1 N HCl. The phases were separated and the water phase was extracted with tert-butyl methyl ether. The organic phases were combined and 140 ml of 10 percent aqueous ammonia solution was added with vigorous stirring within 10 minutes. After 1 hour, the phases were separated, dried with $Na_2SO_4$ and concentrated by evaporation. The residue was distilled in a vacuum (0.1 mbar). There was a yield of 63.7 g of benzoylacetic acid ethyl ester with a purity of 97.1 percent, corresponding to 78 percent of theory. The boiling point of the product was 85° C./0.1 mbar.

EXAMPLE 2

Pivaloylacetic acid methyl ester
(4,4-dimethyl-3-oxopentanoic acid methyl ester)

51.7 g (0.2 mol) of acetoacetic acid methyl ester magnesium enolate in 730 ml of tetrahydrofuran was suspended under nitrogen, 24.3 g (0.24 mol) of triethylamine was added and 49.2 g (0.408 mol) of pivaloyl chloride was instilled in 10 minutes. The reaction mixture was refluxed for 2 hours, cooled and hydrolyzed with 280 ml of 1 N HCl. The phases were separated and the water phase was extracted with tert-butyl methyl ether. The organic phases were combined and 138 ml of 10 percent ammonia solution was added with vigorous stirring within 10 minutes. After 1 hour, the phases were separated, dried with $Na_2SO_4$ and concentrated by evaporation. The residue was distilled in a vacuum (13 mbars). There was a yield of 52.4 g of methyl pivaloylacetate with a purity of 97.8 percent, corresponding to 81 percent of theory. The boiling point of the product was 55° C./13 mbars.

EXAMPLE 3

4-Chlorobenzoylacetic acid ethyl ester 28.8 g (0.1 mol) of acetoacetic acid ethyl ester magnesium enolate in 375 ml of tetrahydrofuran was suspended under nitrogen, 12.2 g (0.12 mol) of triethylamine was added and 35.7 g (0.204 mol) of 4-chlorobenzoyl chloride was instilled in 15 minutes. The reaction mixture was refluxed for 2 hours, cooled with ice water and hydrolyzed with 145 ml of 1 N HCl. The phases were separated and the water phase was extracted with tert-butyl methyl ether. The organic phases were combined and 70 ml of 10 percent ammonia solution was added with vigorous stirring within 15 minutes. After 1 hour, the phases were separated, dried with sodium sulfate and concentrated by evaporation. The residue solidified while standing. The product was recrystallized from ethyl acetate/hexane. There was a yield of 39.0 g of 4-chlorobenzoylacetic acid ethyl ester, corresponding to 86 percent of theory. The melting point of the product was 37° to 38° C.

EXAMPLE 4

2,4,5-Trifluorobenzoylacetic acid ethyl ester 7.2 g (0.025 mol) of acetoacetic acid ethyl ester magnesium enolate in 100 ml of tetrahydrofuran was suspended under nitrogen, 3.1 g (0.03 mol) of triethylamine was added and 10.0 g (0.05 mol) of 2,4,5-trifluorobenzoyl chloride was instilled in 10 minutes. The reaction mixture was refluxed for 2 hours, cooled with ice water and hydrolyzed with 40 ml of 1 N HCl. The phases were separated and the water phase was extracted with tert-butyl methyl ether. The organic phases were combined and 20 ml of 10 percent ammonia solution was added with vigorous stirring within 10 minutes. After 1 hour, the phases were separated, dried with sodium sulfate and concentrated by evaporation. The residue was distilled in a vacuum (0.08 mbar). There was a yield of 10.6 g of 2,4,5-trifluorobenzoylacetic acid ethyl ester with a purity of 98.0 percent, corresponding to 84 percent of theory. The boiling point of the product was 90° C./0.08 mbar.

EXAMPLE 5

3-Oxo-5-ohenyl-4-pentenoic acid ethyl ester 28.8 g (0.1 mol) of acetoacetic acid ethyl ester magnesium enolate in 375 ml of tetrahydrofuran was suspended under nitrogen, 12.2 g (0.12 mol) of triethylamine was added and 34.7 g (0.208 mol) of cinnamic acid chloride was instilled in 15 minutes. The reaction mixture was refluxed for 2 hours, cooled with ice water and hydrolyzed with 145 ml of 1 N HCl. The phases were separated and the water phase was extracted with tert-butyl methyl ether. The organic phases were combined and 70 ml of 10 percent ammonia solution was added with vigorous stirring within 15 minutes. After 1 hour, the phases were separated, dried with sodium sulfate and concentrated by evaporation. The residue was distilled in a water jet vacuum (13 mbars). There was a yield of 23.5 g of 3-oxo-5-phenyl-4-pentenoic acid ethyl ester, corresponding to 54 percent of theory. The boiling point of the product was 140° to 142° C./13 mbars.

EXAMPLE 6

3-Oxovaleric acid methyl ester 51.7 g (0.2 mol) of acetoacetic acid methyl ester magnesium enolate in 750 ml of tetrahydrofuran was suspended under nitrogen, 24.3 g (0.24 mol) of triethylamine was added and 38.9 g (0.408 mol) of propionyl chloride was instilled in 15 minutes. The reaction mixture was refluxed for 2 hours, cooled with ice water and hydrolyzed with 285 ml of 1 N HCl. The phases were separated and the water phase was extracted with tert-butyl methyl ether. The organic phases were combined and 140 ml of 10 percent ammonia solution was added with vigorous stirring within 15 minutes. After 1 hour, the phases were separated, dried with sodium sulfate and concentrated by evaporation. The residue was distilled with a Spaltrohr column (split-tube column) at 100 mbars. There was a yield of 23.9 g of 3-oxovaleric acid methyl ester with a purity of 96.0 percent, corresponding to 44 percent of theory. The acetoacetic acid methyl ester separated as the first runnings was able to be used again. The yield thus increased, relative to reacted acetoacetic acid methyl ester, to 69 percent. The

EXAMPLE 7

3-Oxovaleric acid ethyl ester 28.8 g (0.1 mol) of acetoacetic acid ethyl ester magnesium enolate in 350 ml of tetrahydrofuran was suspended under nitrogen, 12.2 g (0.12 mol) of triethylamine was added and 18.8 g (0.204 mol) of acryloyl chloride was instilled in 15 minutes. The reaction mixture was refluxed for 2 hours, cooled with ice water and hydrolyzed with 75 ml of 1 N HCl. The phases were separated and the water phase was extracted with tert-butyl methyl ether. The organic phases were combined and 70 ml of 10 percent ammonia solution was added with vigorous stirring within 15 minutes. After 1 hour, the phases were separated, dried with sodium sulfate and concentrated by evaporation. The residue was distilled in a water jet vacuum (18 mbars). There was a yield of 17.0 g of 3-oxo-4-pentenoic acid ethyl ester with a purity of 95.8 percent, corresponding to 57 percent of theory. The boiling point of the product was 78 to 80° C./18 mbars.

EXAMPLE 8

Benzoylacetic acidtert-butyl ester 34.4 g (0.1 mol) of acetoacetic acidtert-butyl ester magnesium enolate in 200 ml of tetrahydrofuran was suspended under nitrogen, 12.2 g (0.12 mol) of triethylamine was added and 29.0 g (0.24 mol) of benzoyl chloride was instilled in 15 minutes. The reaction mixture was refluxed for 2 hours, cooled with ice water and hydrolyzed with 150 ml of 1 N HCl. The phases were separated and the water phase was extracted with tert-butyl methyl ether. The organic phases were combined and 70 ml of 10 percent ammonia solution was added with vigorous stirring within 15 minutes. After 1 hour, the phases were separated, dried with sodium sulfate and concentrated by evaporation. The residue was distilled in a vacuum (0.5 mbar). There was a yield of 33.4 g of benzoylacetic acidtert-butyl ester with a purity of 97.4 percent, corresponding to 74 percent of theory. The boiling point of the product was 106 to 108° C./0.5 mbar.

EXAMPLE 9

Pivaloylacetic acid benzyl ester 41.5 g (0.1 mol) of acetoacetic acid benzyl ester magnesium enolate in 375 ml of tetrahydrofuran was suspended under nitrogen, 12.2 g (0.12 mol) of triethylamine was added and 24.9 g (0.204 mol) of pivaloyl chloride was instilled in 15 minutes. The reaction mixture was refluxed for 2 hours, cooled with ice water and hydrolyzed with 150 ml of 1 N HCl. The phases were separated and the water phase was extracted with tert-butyl methyl ether. The organic phases were combined and 70 ml of 10 percent ammonia solution was added with vigorous stirring within 15 minutes. After 1 hour, the phases were separated, dried with sodium sulfate and concentrated by evaporation. The residue was distilled in a vacuum (10 mbars). There was a Yield of 37.2 g of pivaloylacetic acid benzyl ester with a purity of 98.2 percent, corresponding to 78 percent of theory. The boiling point of the product was 156° to 158° C./10 mbars.

EXAMPLE 10

Benzoylacetic acid ethyl ester 19.2 g (0.24 mol) of pyridine was added under nitrogen to a suspension of 57.9 g (0.2 mol) of acetoacetic acid ethyl ester magnesium enolate in 750 ml of tetrahydrofuran and 57.4 g (0.408 mol) of benzoyl chloride was instilled in 10 minutes. The reaction mixture was refluxed for 2 hours, cooled with ice water and hydrolyzed with 285 ml of 1 N HCl. The phases were separated and the water phase was extracted with tert-butyl methyl ether. The organic phases were combined and 140 ml of 10 percent aqueous ammonia solution was added with vigorous stirring within 15 minutes. The reaction mixture was stirred for 1 hour at room temperature, the phases were separated, dried with $Na_2SO_4$ and concentrated by evaporation. The residue was distilled in a vacuum (0.1 mbar). There was a yield of 62.1 g of benzoylacetic acid ethyl ester with a purity of 97.5 percent, corresponding to 79 percent of theory. The boiling point of the product was 85° C./0.1 mbar.

EXAMPLE 11

Production of benzoylacetic acid ethyl ester 29.4 g (0.24 mol) of N,N-dimethylaniline was added under nitrogen to a suspension of 57.9 g (0.2 mol) of acetoacetic acid ethyl ester magnesium enolate in 750 ml of tetrahydrofuran and 57.4 g (0.408 mol) of benzoyl chloride was instilled in 10 minutes. The reaction mixture was refluxed for 2 hours, cooled with ice water and hydrolyzed with 285 ml of 1 N HCl. The phases were separated and the water phase was extracted with tert-butyl methyl ether. The organic phases were combined and 140 ml of 10 percent aqueous ammonia solution was added with vigorous stirring within 15 minutes. The reaction mixture was stirred for 1 hour at room temperature, the phases were separated, dried with $Na_2SC_4$ and concentrated by evaporation. The residue was distilled in a vacuum (0.1 mbar). There was a yield of 59.7 g of benzoylacetic acid ethyl ester with a purity of 97.8 percent, corresponding to 76% of theory. The boiling point of the product was 85° C./0.1 mbar.

EXAMPLE 12

Benzoylacetic acid ethyl ester (Comparison example without adding a tertiary amine)

57.9 g (0.2 mol) of acetoacetic acid ethyl ester magnesium enolate in 700 ml of toluene was suspended under nitrogen, and 57.4 g (0.408 mol) of benzoyl chloride was instilled in 10 minutes. The reaction mixture was stirred for 3 hours at 80.C, cooled with ice water and hydrolyzed by adding 285 ml of 1 N HCl. The phases were separated and the water phase was extracted with toluene. The organic phases were combined, dried with $MgSO_4$ and concentrated by evaporation. The residue was distilled in a vacuum (0.1 mbar). There was a yield of 33.2 g of benzoylacetic acid ethyl ester with a purity of 74.0 percent, corresponding to 32 percent of theory. It was not possible to separate out the by-product 2-acetylacetoacetic acid ethyl ester by distillation.

EXAMPLE 13

Pivaloylacetic acid methyl ester (Comparison example without adding a tertiary amine)

51.7 g (0.2 mol) of acetoacetic acid methyl ester magnesium enolate in 700 ml of toluene was suspended under nitrogen and 49.2 g (0.408 mol) of pivaloyl chloride was instilled in 10 minutes. The reaction mixture was stirred for 3 hours at 80° C., cooled with ice water and hydrolyzed by adding 280 ml of 1 N HCl. The phases were separated and the water phase was extracted with toluene. The organic phases were combined, dried with $MgSO_4$ and concentrated by evaporation. The residue was distilled in a vacuum (13 mbars). There was a yield of 29.2 g of pivaloylacetic acid methyl ester with a purity of 78.4 percent, corresponding to 36 percent of theory. It was not possible to separate further the by-product 2-acetylacetoacetic acid methyl ester by distillation.

What is claimed is:

1. Process for the production of a 3-oxocarboxylic acid ester of the general formula:

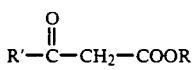 (1)

wherein which R means:
- a straight-chain or branched alkyl radical with 1 to 20 C atoms,
- an alkenyl or alkinyl radical with 3 to 6 C atoms,
- a cycloalkyl radical,
- an ethyl radical substituted with an alkoxy group with 1 to 4 C atoms,
- an alkyl or alkenyl radical with 1 to 4 C atoms substituted with an optionally substituted phenyl group, or
- an optionally substituted aryl radical, and R' means:
- a straight-chain or branched alkyl radical with 1 to 20 C atoms, which can be substituted by at least one halogen, at least one lower alkoxy group, lower alkylthio group, an optionally-substituted aryl, a cycloalkyl, an aryloxy, an arylthio or at least one saturated or unsaturated heterocycle, excluding unsubstituted methyl,
- a straight-chain or branched alkenyl radical with 2 to 20 C atoms, which can be substituted by at least one halogen or an aryl,
- an alkinyl radical, which can be substituted by aryl,
- an optionally substituted cycloalkyl or cycloalkenyl radical,
- an optionally substituted monocyclic or polycyclic aryl radical, or
- an optionally substituted saturated or unsaturated monocyclic or polycyclic heterocyclic radical, comprising acylating of the magnesium enolate of a corresponding acetoacetic acid ester of the general formula:

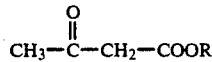 (2)

with a corresponding carboxylic acid chloride of the general formula:

 (3)

to a corresponding 2-acylacetoacetic acid ester of the general formula:

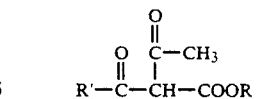 (4)

wherein in each case R and R' have the above-mentioned meanings, the acylation being performed in the presence of a tertiary amine, and subsequently cleaving the acetyl group.

2. Process according to claim 1 wherein a compound selected from the group consisting of trialkylamines with the same or different straight-chain, branched or cyclic alkyl radicals, N-alkylpyrrolidines, N-alkylpiperidines, N-alkylmorpholines, alkyl(arylalkyl)amines, arylalkylamines, quinuclidine, 1,4-diazabicyclo[2.2.2]octane, pyridine, quinoline, alkylpyridines, 4-dialkylaminopyridines, 1,5-diazabicyclo[4.3.0]non-5-ene, 1,8-diazabicyclo-[5.4.0]undec-7-ene, and a mixture of at least two of these compounds, is used as the tertiary amine.

3. Process according to claim 2 wherein a trialkylamine is used as the tertiary amine.

4. Process according to claim 3 wherein triethylamine is used as the trialkylamine.

5. Process according to claim 4 wherein, relative to 1 mol of acetoacetic acid ester magnesium enolate, the carboxylic acid chloride is used in an amount of 2.0 to 2.5 mol and the triethylamine is used in an amount of 1.0 to 1.4 mol.

6. Process according to claim 5 wherein the acylation of the acetoacetic acid ester magnesium enolate is performed in an aliphatic or aromatic hydrocarbon, an open-chain or cyclic ether or a mixture of such compounds, as a solvent.

7. Process according to claim 6 wherein tetrahydrofuran is used as the solvent.

8. Process according to claim 7 wherein the acylation of acetoacetic acid ester magnesium enolate is performed at a temperature of 20° to 140° C.

9. Process according to claim 8 wherein the acylation is performed at a temperature of 60° to 90° C.

10. Process according to claim 9 wherein the cleavage of the acetyl group takes place with a base selected from the group consisting of ammonia, primary amines and secondary amines.

11. Process according to claim 10 wherein the cleavage of the acetyl group takes place with aqueous ammonia.

12. Process according to claim 1 wherein the acylation of the acetoacetic acid ester magnesium enolate is performed in an aliphatic or aromatic hydrocarbon, an open-chain or cyclic ether or a mixture of such compounds, as a solvent.

13. Process according to claim 12 wherein tetrahydrofuran is used as the solvent.

14. Process according to claim 1 wherein the acylation of acetoacetic acid ester magnesium enolate is performed at a temperature of 20° to 140° C.

15. Process according to claim 14 wherein the acylation is performed at a temperature of 60° to 90° C.

16. Process according to claim 1 wherein the cleavage of the acetyl group takes place with a base selected from the group consisting of ammonia, primary amines and secondary amines.

17. Process according to claim 16 wherein the cleavage of the acetyl group takes place with aqueous ammonia.

* * * * *

UNITED STATES PATENT AND TRADEMARK OFFICE
CERTIFICATE OF CORRECTION

PATENT NO. : 5,144,057
DATED : Sep. 1, 1992
INVENTOR(S) : Martin Eyer

It is certified that error appears in the above-identified patent and that said Letters Patent is hereby corrected as shown below:

On the title page: Item

[30]  Foreign Application Priority Data

October 15, 1990 [CH]  Switzerland ........... 3301/90

Signed and Sealed this

Fifth Day of October, 1993

Attest:

BRUCE LEHMAN

Attesting Officer

Commissioner of Patents and Trademarks